United States Patent [19]

Cohen

[11] Patent Number: 5,518,720
[45] Date of Patent: May 21, 1996

[54] TREATMENT OF COMPLICATIONS OF DIABETES WITH SUBSTANCES REACTIVE WITH THE FRUCTOSYL-LYSINE STRUCTURE IN GLYCATED ALBUMIN

[75] Inventor: Margo P. Cohen, New York, N.Y.

[73] Assignee: Exocell, Inc., Philadelphia, Pa.

[21] Appl. No.: 215,662

[22] Filed: Mar. 22, 1994

Related U.S. Application Data

[63] Continuation of Ser. No. 998,921, Dec. 30, 1992, abandoned.

[51] Int. Cl.$^6$ .......................... A61K 39/395; C07K 16/18
[52] U.S. Cl. ..................... 424/137.1; 424/130.1; 424/134.1; 424/145.1; 530/387.5; 530/388.25
[58] Field of Search .................. 424/9, 130.1, 134.1, 424/137.1, 141.1, 145.1; 435/7.1, 387.5, 70.21, 172.2, 240.27; 530/387.5, 388.25; 514/2, 8

[56] References Cited

U.S. PATENT DOCUMENTS

| | | | |
|---|---|---|---|
| 4,797,473 | 1/1989 | Tarsio et al. | 530/387 |
| 5,173,422 | 12/1992 | Knowles et al. | 435/240.27 |

FOREIGN PATENT DOCUMENTS

| | | | |
|---|---|---|---|
| 8906798 | 7/1989 | WIPO | G01N 33/53 |

OTHER PUBLICATIONS

Hud & Cohen Clincy Chimicaacta 185:157–164 (1989).
Joliffe Intern Rev. Immunol 10:241–50 (1993).
Castano et al. Ann Rev Immunol 8:647–79 (1990).
Sabbatini et al. Kidney Intl. 42:875–881 (1992).
Predescu et al. J Cell Biol 107: 1729–1738 (1988).
Witzum et al. PNAS 81: 3204–3208 (1984).
Mountain et al. Biotech Gen Eng Rev 10, pp. 1 10–13 (1992).
Merckmanual pp. 1106–1107 16th Ed. 1992.
Van Brunt Bioworld Financial Watch 3:1–9 (1995).
Waldmann Science 252: 1657–1662 (1991).
Dillman Annals Int. Med 111: 592–603 (1989).
Harris et al. Tibtech 11: 42–44 (1993).
The Green Sheet 1003; 42(28)2–3.
The Pink Sheet 1991; 43(35:T&G–10–11.
The Gray Sheet 1993; 19(23):I&W–8–I&W–9.
The Green Sheet 1993; 42(3):1.
The Pink Sheet, Nov. 2, 1987.
Hygeia Pharmaceuticals, Inc. Advertisement (1992).
Cambridge Antibody Technology Ltd. Advertisement.
Beck, et al., "Brief Report: Alleviation of Systematic Manifestations of Castleman's Disease by Monoclonal Anti--Interleukin-6 Antibody", *The New England Journal of Medicine*, 330(9):602–605 (1994).
The Pink Sheet 1994; 56(3):8–91.

Vuillez, et al., "Immunoscintigraphy Using $^{111}$In–Labeled F(ab')hd 2 Fragments of Anticarcinoembryonic Antigen Monoclonal Antibody for Detecting Recurrences of Medullary Thyroid Carcinoma", *J. Clin. Endo. and Metabolism*, 74(1):157–163 (1992).
Serafini, "Biocompatible MoAbs Detect, Stage Disease", *Diagnostic Imaging*, pp. 94–98, Jun. 1990.
Riechmann, et al., "Reshaping Human Antibodies for Therapy", *Nature*, 332:323–327 (1988).
Saragovi, et al., "Design and Synthesis of a Mimetic from an Antibody Complementarity–Determining Region", *Science*, 253:792–794 (1991).
Mayforth, et al., "Designer and Catalytic Antibodies", *New England Journal of Medicine*, 323(3):173–178 (1990).
Kaminski, et al., "Radioimmunotherapy of B–Cell Lymphoma with [$^{131}$I]Anti–B1 (Anti–CD20) Antibody", *New England Journal of Medicine*, 329:(7):459–465 (1993).
Steplewski, et al., "Biological Activity of Human–Mouse IgG1, IgG2 IgG3, IgG4 Chimeric Monoclonal Antibodies with Antitumor Specificity"*Proc. Natl. Acad. Sci. USA*, 85:4852–4856 (1988).
Sun, et al., "Chimeric Antibody with Human Constant Regions and Mouse Variable Regions Directed Against Carcinoma–Associated Antigen 17–1A", *Proc. Natl. Acad. Sci. USA*, 84:214–218 (1987).
Wolff, et al., "The Use of Digoxin–Specific Fab Fragments for Severe Digitals Intoxication in Children", *New England Journal of Medicine*, 326(26):1739–1744 (1992).
Press, et al., "Radiolabeled Antibody Therapy of B–cell Lymphoma with Autologous Bone Marrow Support", *New England Journal of Medicine*, 329(17):1219–1224 (1993).
Cohen, et al., "Production and Characterization of Monoclonal Antibodies Against Human Glycoalbumin", *J. Immunol. Methods*, 117:121–129 (1989).
Kelley, et al., "A Method for Localizing the Early Products of Nonenzymatic Glycosylation in Fixed Tissue," *J. Investigative Dermatology*, 93(3):327–331 (1989).
Michael, et al., "Incresaed Concentration of Albumin in Kidney Basement Membranes in Diabetes Mellitus", *Diabetes*, 30:843–846 (1981).

(List continued on next page.)

*Primary Examiner*—Margaret Parr
*Assistant Examiner*—Phillip Gambel

[57] ABSTRACT

Methods of in vivo diagnosis and treatment for complications of diabetes are provided. Antibodies or other mimetic molecules which specifically bind to glycated albumin or its cellular receptor are administered to a human. Glycated albumin which retains a deoxyfructosyllysine moiety is found deposited at sites of diabetic tissue damage. Glycated albumin inhibits the growth of cells. Treatment with monoclonal anti-glycated albumin antibody reverses the growth inhibition caused by glycated albumin. In addition, glycated albumin stimulates the production of type IV collagen by kidney cells. Antibodies which bind to glycated albumin prevent the stimulation of type IV collagen production.

9 Claims, 1 Drawing Sheet

OTHER PUBLICATIONS

Shaklai, et al., "Nonenzymatic Glycosylation of Human Serum Albumin Alters Its Conformation and Function", *J. Biol. Chem.*, 259(6):3812–3817.

Williams, et al., "Preferential transport of Non–Enzymatically Glucosylated Ferritin Across the Kidney Glomerulus", *Kidney International*, 28:146–152 (1985).

Brownlee, et al., "Covalent Attachment of Soluble Proteins by Nonenzymatically Glucosylated Collagen", *J. Exp. Med.*, 158:1739–1744 (1983).

Vaughn, et al., "Diabetes, Autoimmunity, and Arteriosclerosis", *Clin. Immun. and Immunpath.*, 52:414–420 (1989).

Brownlee, et al., "Nonenzymatic Glycosylation Products on Collagen Covalently Trap Low–Density Lipoprotein", *Diabetes*, 34:938–941 (1985).

Miller, et al., "Immunopathology of Renal Extracellular Membranes in Diabetes Mellitus", *Diabetes*, 25:(8):701–708 (1976).

Williams, et al., "Enhanced Vesicular Ingestion of Nonenzymatically Glycosylated Proteins by Capillary Endothelium", *Microvascular Research*, 28:311–321 (1984).

Williams et al., "Micropinocytic Ingestion of Glycosylated Albumin by Isolated Microvessels: Possible Role in Pathogenesis of Diabetic Microangiopathy", *Proc. natl. Acad. Sci. USA*, 78(4):2393–2397 (1981).

Smith, et al., "Premeability and Mechanism of Albumin, Cationized Albumin, and Glycosylated Albumin Transcellular Transport Across Monolayers of Cultured Bovine Brain Capillary Endothelial Cells", *Pharm. Res.*, 6(6):466–473 (1989).

McVerry, et al., "Production of Psuedodiabetic Renal Glomerular Changes in Mice After Repeated Injections of Glucosylated Proteins,", *The Lancet*, 1(8171):738–740 (1980).

Aggarwal, et al., "Increased Uptak eof Glycated Albumin by Glomerular Mesangial and Epithelial Cells In Situ is Accompanied by Augmented Local Production of $H_2O_2$: Studies Utilizing Confocal Microscopy," *Clin. Res.*, 40:179A (1992).

TREATMENT OF COMPLICATIONS OF DIABETES WITH SUBSTANCES REACTIVE WITH THE FRUCTOSYL-LYSINE STRUCTURE IN GLYCATED ALBUMIN

This application is a continuation-in-part of application Ser. No. 07/998,921, filed Dec. 30, 1992, now abandoned.

TECHNICAL FIELD OF THE INVENTION

This invention is related to the in vivo visualization of tissues and organs to determine complications of diabetes. It is also related to the treatment of diabetic complications with substances reactive with the fructosyllysine group in non-enzymatically glycated albumin. The invention further relates to the cell recognition site of fructosyllysine in non-enzymatically glycated albumin.

BACKGROUND OF THE INVENTION

Nonenzymatic glycation of albumin, the major serum protein, is a structural modification that can affect the biologic properties of albumin and increase the susceptibility of diabetic subjects to kidney and other complications of diabetes.

Nonenzymatic glycation is a condensation reaction between carbohydrate and free amino groups at the amino-terminus of proteins or at the epsilon amino groups of lysine residues of proteins. The reaction is initiated with attachment of the aldehyde function of acyclic glucose to a protein amino group via nucleophilic addition, forming an aldimine, also known as a Schiff base. This intermediate product subsequently undergoes an Amadori rearrangement to form a 1-amino-1-deoxyfructose derivative in stable ketoamine linkage, which in turn can cyclize to a ring structure (Cohen M. P., *Diabetes and Protein Glycosylation*, Springer Verlag, 1986). This bimolecular condensation of free saccharide with protein constitutes a mechanism by which proteins are subject to post-ribosomal modification without the influence of enzymatic activities. In diabetic subjects, hyperglycemia promotes increased nonenzymatic glycation of circulating and tissue proteins, which has allowed the assessment of integrated glycemic control through determination of circulating glycated protein levels. The increased glycation of proteins may also provide insight into the pathogenetic mechanisms responsible for the chronic complications associated with diabetes.

Experimental studies have suggested several ways in which glycation of albumin could theoretically contribute to the development of kidney and other complications associated with diabetes. These include the induction of conformational changes and alterations in the ligand binding properties of albumin (Shaklai, et al., *J. Biol. Chem.* 259:3812, 1984), and the induction of enhanced transendothelial passage of albumin (Williams, et al., *Proc. Natl. Acad. Sci. USA*, 78:2393, 1981; Williams & Solenski, *Microvasc. Res.* 28:311, 1984; Williams & Siegal, *Kid. Int.* 28:146, 1985). Such experimental studies have used albumin glycated in vitro to explore effects on its biological properties. Deposition of glycated albumin in extracellular matrices (Miller, et al., *Diabetes*, 25:701, 1976; Michael & Brown, *Diabetes* 30:843, 1981; McVerry, et al., *Lancet* 2:738, 1980), and the formation of advanced glycation end products (Cohen, M P, supra, 1986) also have been suggested to be involved in the development of kidney disease and other complications.

Electron microscopic work indicates that nonenzymatically glycated albumin is taken up more avidly than native albumin by endothelial cells. Endothelial cell uptake involves micropinocytic vesicles which participate in the bidirectional transport of proteins across the capillary wall. Additionally, glycation promotes the preferential transport of albumin across the glomerular filtration barrier. Carbohydrate-free protein perfused into kidneys accumulates within the lamina rara interna and is restricted from transglomerular passage, whereas glycated protein penetrates the lamina densa and the lamina rara externa and accumulates in epithelial pinocytic vesicles and multivesicular bodies. The increased capillary permeability in diabetes has been ascribed, in part, to the increase in transendothelial transport that glycation of albumin confers. This increased transport and facilitated penetration of the basement membrane may cause deposition of glycated albumin in the subendothelial face of the filtration barrier and in the appositioned cellular elements. Other studies have suggested that glycated albumin may accumulate in and/or injure tissues by binding to proteins in the cell or matrix (Brownlee, et al., *Diabetes* 34:938, 1985; *J. Exp. Med.* 158: 1739, 1983) and by forming immune complexes (Vaughn, et al., *Clin. Immunol. and Immunopath.* 52:414, 1989) or advanced glycation end products (Cohen, M P, supra, 1986). Also, the injection of glycated plasma proteins has been reported to produce glomerular basement membrane thickening in nondiabetic mice (McVerry, et al., *Lancet* 2:738, 1980) and hyperfiltration in nondiabetic rats (Sabbatini, et al., *Kid. Int.* 42:875, 1992).

Histochemical studies have suggested that endogenous albumin can bind to kidney basement membrane (Miller, et al., *Diabetes* 25:701, 1976) and that there is increased deposition of albumin in the basement membranes of patients with diabetic nephropathy (Michael, et al., *Diabetes* 30:843, 1981). However, such studies did not distinguish between glycated and unglycated albumin. Even if glycated albumin does accumulate in kidneys or other tissues in diabetic subjects, it is not known whether the deposited glycated albumin retains its fructosyllysine chemical configuration. In fact, prior art has suggested that the fructosyllysine group of glycated albumin that is deposited in tissues is obscured through the formation of advanced glycation end products and cross-links (Brownlee, et al., *Science* 232:1629, 1989).

Thus, there is a need in the art to determine whether glycated albumin accumulates in the kidneys and other tissues of diabetic subjects and to determine whether detection of accumulated glycated albumin can be used to determine the course of treatment. There is also a need in the art for a means to prevent the deleterious cell and tissue effects of glycated albumin that contribute to the development of complications of diabetes.

SUMMARY OF THE INVENTION

It is an object of the invention to provide a method for assessing the localization of glycated proteins in microvascular tissues.

Another object of the invention is to provide a method for treating complications of diabetes which are caused by glycated albumin.

It is yet another object of the invention to provide a method for treating complications of diabetes which are caused by glycated albumin.

Another object of the invention is to provide an antibody which specifically binds to a cellular receptor for glycated albumin.

These and other objects of the invention are achieved by providing a method for assessing the localization of glycated proteins in microvascular tissues comprising the steps of: parenterally administering to a human a diagnostic molecule capable of specifically reacting with N-deoxyfructosyllysine in glycated albumin, said diagnostic molecule bearing a detectable label; and determining the location of the detectable label in the human.

Another embodiment of the invention achieves the objects of the invention by providing a method of treating complications of diabetes which are caused by glycated albumin, comprising the step of: parenterally administering to a diabetic patient a therapeutic molecule capable of specifically reacting with N-deoxyfructosyllysine in glycated albumin.

Another embodiment of the invention achieves the objects of the invention by providing a method of treating complications of diabetes which are caused by glycated albumin comprising the step of administering to a diabetic patient a therapeutic molecule capable of specifically preventing the reaction of glycated albumin with its cell recognition site.

In yet another embodiment of the invention, an isolated antibody is provided which specifically binds to kidney mesangial cell membrane proteins having a molecular weight selected from the group consisting of about 78, 110 and 205 kd, said proteins specifically binding glycated albumin but not binding non-glycated albumin. The present invention thus provides the art with powerful diagnostic and therapeutic methods and molecules for determining and treating complications of diabetes.

DETAILED DESCRIPTION

Figure 1:
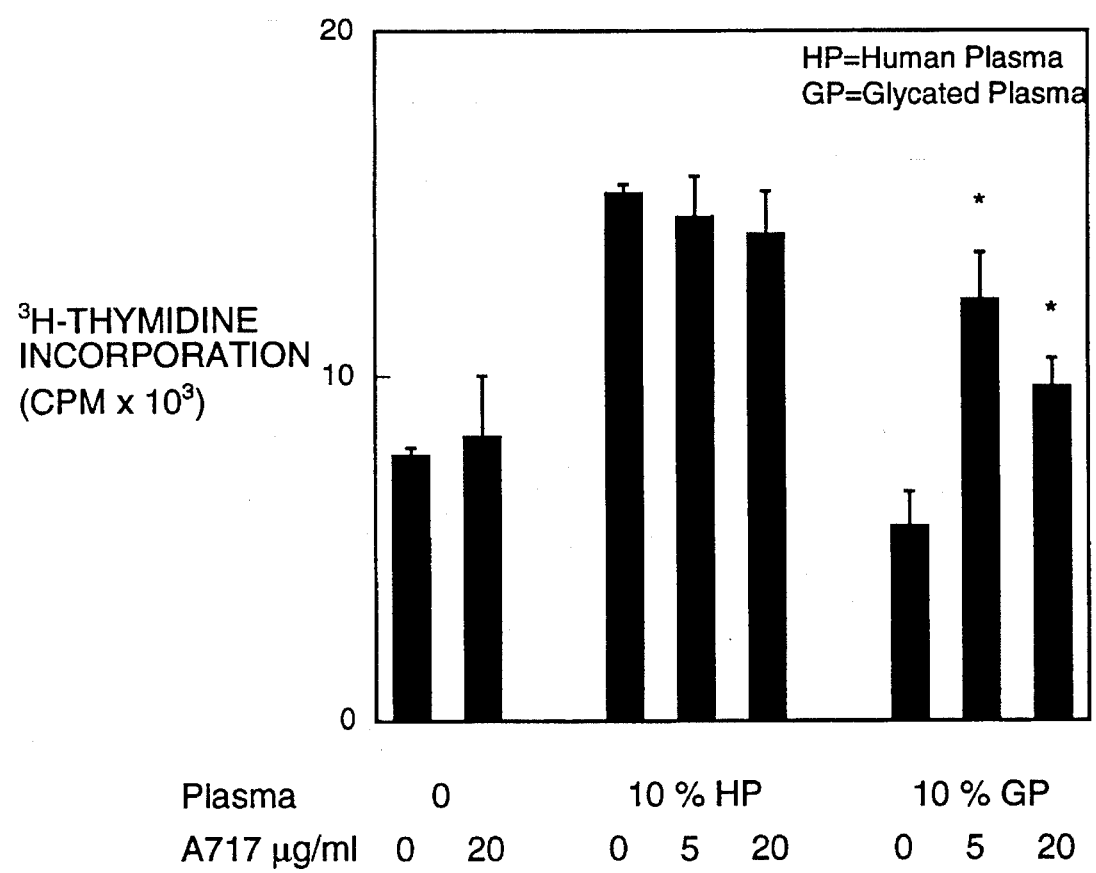
FIG. 1 shows the inhibitory effect of glycated albumin on growth of kidney cells. Addition of antibodies that selectively recognize glycated epitopes on albumin reverses the effect.

It is a finding of the present invention that diabetics not only display increased levels of glycated albumin in their plasma, but also display increased levels of glycated albumin in their solid tissues. The increased levels are detected as accumulations of glycated albumin in loci of diabetic complications. Sites of diabetic complications where accumulation may be observed are microvascular tissues which include kidneys, nerves, eyes, and blood vessels. On the basis of this finding, methods are provided for monitoring diabetic complications which involve the in vivo detection of glycated albumin in the human body. Kidneys are often the site of diabetic tissue damage. The present invention allows the determination of glycated albumin deposition in kidneys as well as in other organs and tissues.

Moreover, it has now been discovered that glycated albumin has specific physiological effects. It inhibits growth of cells, such as kidney cells. It also causes increased production of collagen by kidney cells. These may be the mechanisms by which diabetes damages tissues. These findings suggest that the monitoring of glycated albumin in tissues of the body can indicate when and where damage will occur. In addition, these findings suggest that prevention or reversal of such cellular abnormalities and tissue damage can be effected by binding of glycated albumin. In fact, it has now been discovered that administration of molecules which bind glycated albumin counteracts the growth-inhibitory and collagen-stimulatory effects of glycated albumin on cells.

It is a further discovery of the present invention that glycated albumin binds to a specific site (receptor) on the membranes of kidney cells. This binding may be the mechanism by which glycated albumin induces the cellular abnormalities described above. Molecules which prevent the binding of glycated albumin to its receptor can counteract the growth-inhibitory and collagen-stimulatory effects of glycated albumin on cells.

Molecules which can be administered to humans for diagnostic or therapeutic uses include those which are capable of specifically reacting with N-deoxyfructosyllysine in glycated albumin. Such molecules may be antibodies which immunoreact with an epitope present on glycated albumin but not present on albumin or other human proteins. One such antibody is A717, which is made by a nybridoma which is made by a nybridoma which has been deposited at the American Type Culture Collection, 12301 Parklawn Drive, Rockville, Md. 20852 as accession No. HB 9596 on Dec. 2, 1987. Other antibodies with similar specificity can, of course, be readily obtained and used. Patent application Ser. No. 147,363, the disclosure of which is expressly incorporated herein, teaches methods of obtaining other antibodies with similar properties. Alternatively, fragments of antibodies such as F(ab')$_2$ and Fab can be used. Anti-idiotypic antibodies which contain a binding site homologous to the epitope recognized by the A717 antibodies can also be used according to the present invention. In addition, other substances having homologous structures to the combining site of the antibody A717 can be used. For example, synthetic peptides derived from the complementarity determining region of the hypervariable domain of an antibody specifically reactive with glycated albumin can be used. Similarly, non-peptide compounds of designed specificities and conformational restrictions which mimic the binding and functional properties of a glycated albumin-specific monoclonal antibody can be used. Synthetic peptides derived from the complementarity determining region of the hypervariable domain of an anti-idiotypic antibody specifically reactive with the reactive domain of the A717 antibody can be used for their ability to substitute for binding of glycated albumin to its cell receptor, as can the anti-idiotypic antibodies themselves. Similarly, non-peptide compounds of designed specificities and conformational restrictions which mimic the binding and functional properties of an anti-glycated albumin specific anti-idiotypic monoclonal antibody can be used. Antibodies which specifically bind to the cell membrane receptor for glycated albumin can be readily produced according to any of the techniques for raising antibodies which are known in the art. The antibody can be monoclonal or polyclonal. If polyclonal it is preferably affinity purified based on its ability to bind to either isolated receptor or to the A717 antibody.

For diagnostic purposes, the diagnostic molecule is preferably detectably labeled. Suitable radioisotopes for such labeling include iodine-131, iodine-123, technetium-99m, and indium-111. Others known in the art to be suitable for such purposes can also be used. Methods for radiolabeling antibodies and other proteins either by direct conjugation or via a chelate are known in the art.

The location of detectable label in the human is determined by any suitable means such as scintiscanning, using known techniques. Such determinations provide an in vivo visualization of the accumulation of glycated albumin in the body. If visualization of a particular organ is desired, then the diagnostic molecule can be administered directly to that region of the body by injecting it into an artery which serves the particular organ, such as the kidneys.

For treatment and preventative purposes, therapeutic molecules, as described above, can be administered to block or titrate the glycated albumin epitopes. By binding to glycated albumin or to its cell recognition site (receptor), the therapeutic molecules can alleviate or reverse the tissue damage which is caused by the accumulation and binding of glycated albumin to its cell receptor.

Administration according to the methods of the present invention are any parenteral method which achieves a sufficient concentration of diagnostic or therapeutic molecule in the targeted region of the body to be diagnostically or therapeutically useful. Typically such administration will be by intravenous or intraarterial infusion, although subcutaneous and intramuscular injections can also be used. Non-peptide compounds may be administered orally. Suitable dosages can be optimized by those of skill in the art by routine testing. Typically concentrations of antibody for therapeutic uses will be between about 1.0 mg and about 10 mg. Concentrations of antibody for diagnostic uses will be between about 0.1 mg and about 1.0 mg. Corresponding concentrations of non-antibody molecules will be used on a mole-mole basis to achieve the same effective concentration of glycated albumin-binding power. Such concentrations can be readily determined based on the size of the molecule.

The present invention employs specific immunologic recognition and reaction between a monoclonal antibody and the antigenic epitope to which the antibody uniquely and specifically binds. The monoclonal antibody is used to target specific molecules in vivo for diagnostic or therapeutic purposes. Medically useful monoclonal antibodies typically are of a single immunoglobulin class, are specific for a certain antigen, exhibit little variation from batch to batch, and can be coupled to various isotopes, drugs or toxins. The antibody must target an identified antigen that is preferentially expressed in pathologic tissue and have minimal reactivity with normal tissue. The antigen should be present in pathologic sites with a higher density than in normal tissue. The antibody must have high specificity for its target, and its avidity and affinity binding constant should be appropriate for its use. The antibody should retain its immunoreactivity if it is conjugated to various drugs, toxins or radioisotopes.

One such antibody which may be used is the A717 monoclonal antibody to glycated albumin and the epitopes of the glycated albumin antigen target. The antigen is present in diabetic tissues in greater amount than in normal tissue. The presence of excess antigen in diabetic tissue is an expression of a pathologic state. The antibody is immunoreactive with an epitope present on glycated albumin but is not reactive with unglycated albumin, nor with other proteins, whether glycated or not. The epitope identified by the antibody used in the present invention is not present on other proteins. Binding by the antibody to the epitope it recognizes on glycated albumin prevents the binding of glycated albumin to its cell recognition site.

The term antibody as used in this invention is meant to include intact molecules as well as fragments thereof, such as for example Fab and F(ab')$_2$ which are capable of binding the epitopic determinant.

The term complementarity-determining region as used in this invention refers to the region of the hypervariable domain of a monoclonal antibody, such as A717, that binds deoxyfructosyllysine in glycated albumin with high affinity and specificity.

The term anti-idiotype as used in this invention is meant to include intact antibodies as well as fragments thereof that are capable of binding the idiotype of monoclonal antibodies such as A717 that bind glycated albumin.

The term mimetic as used in this invention includes peptide or non-peptide compounds of designed specificities having appropriate conformation to mimic the binding and functional properties of a monoclonal antibody, such as A717 which specifically recognizes glycated albumin.

For purposes of the invention, the glycated albumin target may be present in various tissues such as kidney, eye, blood vessels and nerves. The glycated albumin epitope may reside in situ in cells, at the surface of cells or in extracellular matrices such as the glomerular basement membrane. The cell recognition site for glycated albumin (receptor) may be present in various tissues such as kidney, eye, blood vessels, and nerves, and may reside at the surface of cells and/or at intracellular sites.

The following examples are provided:

Example 1. In vivo deposition of glycated albumin in kidney matrix

Cryostat sections were made of renal cortex of kidneys obtained at autopsy from nondiabetic and diabetic persons, and fixed with acetone on microscope slides. After rinsing with phosphate buffered saline, the sections were incubated with 3% hydrogen peroxide to quench endogenous peroxidase for 30 minutes at room temperature, again rinsed with PBS, and then incubated for 1 hour with blocking agent (1% goat serum). After rinsing, the sections were incubated with A717 monoclonal antibody (5 µg/ml) for 1 hour at room temperature, rinsed, then incubated with biotinylated anti-mouse IgG antibody for 20 minutes. Following washing, the sections were incubated with AEC substrate/developing reagent chromogen (3-amino-9-ethylcarbazole substrate in N, N-dimethylformamide) containing 3% hydrogen peroxide for 10 minutes. After rinsing in deionized water and counterstaining with hematoxylin, the sections were examined microscopically.

Normal kidneys revealed no staining with the chromogen, indicating undetectable amounts of glycated albumin in the renal cortex tissue. Diabetic kidneys revealed intense pink chromogen staining in the subendothelial surface of the capillary and tubular basement membranes and in the glomerular mesangium, indicating deposition of glycated albumin in the renal extracellular matrix.

Example 2 Compromise of kidney cell function by glycated albumin

Growth of kidney mesangial cells in culture was assessed by tritiated thymidine incorporation. Cells were passaged and grown to subconfluence for 2 days, rested for 1 day in serum-free medium containing 100 mg/dL glucose, and then grown for 48 hours in medium containing 100 mg/dL glucose and no plasma supplements or supplemented to 3% or 10% with normal plasma or with plasma in which the albumin had been nonenzymatically glycated by incubation for 4 days with 500 mg/dL glucose. At the end of the 48 hour incubation period with unsupplemented or supplemented medium, the cells were pulsed for 8 hours with [$^3$H]-thymidine (Amersham, Arlington Heights, Ill.). Cells were collected on glass microfiber filters using a cell harvester, and radioactivity was assayed after placing the filters in a liquid scintillation counter. [$^3$H]-thymidine incorporation was stimulated in a dose dependent response manner by the addition of normal human plasma (Table 1). However, incorporation was inhibited in a dose-dependent manner when cells were grown in medium supplemented with plasma containing albumin that had been nonenzymatically glycated (Table 1).

TABLE 1

| Supplement | $^3$H-thymidine (cpm/well) |
|---|---|
| 0% | 7750 |
| 3% normal plasma | 12310 |
| 10% normal plasma | 15390 |
| 3% glycated plasma | 10150 |
| 10% glycated plasma | 5690 |

Example 3. Prevention of glycated albumin-induced effects on kidney cell growth by blocking fructosyl-lysine groups Growth of kidney mesangial cells in culture was assessed by tritiated thymidine incorporation as in Example 2. Cells were passaged and grown to subconfluence for 2 days, rested for 1 day in serum free medium containing 100 mg/dL glucose, and then grown for 48 hours in media containing 100 mg/dL glucose without or with supplementation with 10% normal plasma or 10% glycated plasma and 5–20 µg/ml of a monoclonal antibody that selectively recognizes glycated epitopes (fructosyl-lysine) residing in albumin. As shown in FIG. 1, addition of the antibody had no effect on basal incorporation (no added plasma) or on incorporation stimulated by 10% normal plasma, but restored proliferative activity in cells cultured in the presence of glycated plasma containing nonenzymatically glycated albumin.

Example 4. Stimulation of kidney cell collagen production by glycated albumin Kidney mesangial cells in culture were grown for 96 hours in media containing 100 or 450 mg/dL glucose and 3% normal serum or 3% glycated serum in which the albumin had been nonenzymatically glycated by incubation for 5 days with 500 mg/dL glucose. Media also contained 50 µg/ml each of ascorbic acid and β-aminoproprionitrile. Type IV collagen secreted into the medium was measured by enzyme linked immunosorbent assay. The production of type IV collagen was significantly stimulated in the presence of glycated serum.

TABLE 2

| Glucose | Serum Supplement | Type IV Collagen ng/10$^6$ Cells |
|---|---|---|
| 100 mg/dL | normal serum | 112 ± 7 |
| 100 mg/dL | glycated serum | 140 ± 8 |
| 450 mg/dL | normal serum | 111 ± 4 |
| 450 mg/dL | glycated serum | 205 ± 14 |

Example 5. Prevention of glycated albumin-induced effect on kidney cell collagen production by blocking fructosyllysine groups Kidney mesangial cells in culture were grown for 96 hours in media containing 180 mg/dL glucose and 10% normal serum or 10% glycated serum, with or without addition of 5 µg/ml of monoclonal antibody A717 that selectively recognizes glycated epitopes (fructosyllysine) residing in albumin. Addition of antibody had no effect on collagen production in the presence of normal serum, but prevented the glycated serum-induced stimulation of collagen production.

TABLE 3

| Serum Supplement | A717 Antibody | Type IV Collagen µg/10$^6$ Cells |
|---|---|---|
| 10% normal serum | − | 325 ± 8 |
| 10% glycated serum | − | 432 ± 55 |
| 10% normal serum | + | 310 ± 33 |
| 10% glycated serum | + | 274 ± 10 |

Example 6. Stimulation of kidney cell collagen gene transcription by glycated albumin Kidney mesangial cells were grown for 96 hours in media containing 100 or 450 mg/dL glucose, without added serum or with the addition of 3% normal serum or 3% glycated serum in which the albumin had been nonenzymatically glycated by incubation for 5 days with 500 mg/dL glucose. RNA was extracted from the gels, electrophoresed on agarose gels, transferred to nylon membranes, and hybridized with [$^{32}$P]-αCTP probes for type IV collagen and glyceraldehyde phosphate dehydrogenase (GAPDH) genes. The ratio of type IV collagen to GAPDH mRNA, determined by densitometric scanning of the x-ray films (autoradiographs) exposed to the hybridized RNA showed that glycated albumin induces expression of the type IV collagen gene in mesangial cells.

TABLE 4

| Glucose | Serum Supplement | Type IV Collagen:GAPDH mRNA Ratio |
|---|---|---|
| 100 mg/dL | — | .491 |
| 100 mg/dL | 3% normal serum | .735 |
| 100 mg/dL | 3% glycated serum | .887 |
| 450 mg/dL | — | 3.21 |
| 450 mg/dL | 3% normal serum | 17.66 |
| 450 mg/dL | 3% glycated serum | 51.25 |

Example 7. Glycated albumin bound by a specific cell recognition site

Kidney mesangial cells were lysed by freeze/thaw and centrifuged to obtain the cell membranes, which were extracted with CHAPS (3-[3-cholamidopropyl) dimethylaminonio- 1-propanesulfonate). The detergent-solubilized mesangial cell membrane extract was applied to an affinity chromatography column containing glycated albumin immobilized to Sepharose™. The adsorbed protein, which represents cell membrane proteins capable of specific binding to glycated albumin were eluted with 3M sodium thiocyanate, and subjected to SDS-polyacrylamide gel electrophoresis followed by transfer to nitrocellulose. The transfers were incubated with glycated albumin or with nonglycated albumin, and the binding of the albumin preparations to mesangial cell proteins on the electrophoretic transfers were detected by incubation with an anti-albumin antibody conjugated to horseradish peroxidase. A membrane protein of approximately 60,000 molecular weight bound both glycated albumin and non-glycated albumin. In contrast, membrane proteins of approximately 78 kd and 110 kd molecular weight specifically bound glycated albumin. Another membrane protein of about 205 kd, which specifically binds glycated albumin also was faintly detectable.

Example 8. Prevention of glycated albumin binding to its cell recognition site by blocking fructosyllysine groups Mesangial cell membrane proteins are extracted and separated by affinity chromatography, followed by electrophoresis and transfer to nitrocellulose as in Example 6. The transfers are incubated with glycated albumin with or without the addition of monoclonal antibody A717. Detection with horseradish peroxidase conjugated anti-albumin is as in Example 6. The binding of glycated albumin to the 60,000 molecular weight membrane protein is not affected by the monoclonal antibody, whereas the binding of glycated albumin to the approximately 78 kd and 110 kd molecular weight mesangial cell membrane proteins is prevented by the A717 monoclonal antibody.

I claim:

1. A method of treating complications of diabetes which are caused by glycated albumin, comprising the steps of:
    parenterally administering to a diabetic patient a therapeutic molecule which specifically binds the glycated albumin epitope bound by the monoclonal antibody produced by cell line ATCC HB 9596.

2. The method of claim 1 wherein the therapeutic molecule is a monoclonal antibody which specifically binds to an epitope present on glycated albumin but not present on non-glycated albumin or other human proteins.

3. The method of claim 2 wherein the antibody is A717 (produced by ATCC Deposit HB 9596).

4. The method of claim 1 wherein the patient has kidney disease.

5. The method of claim 4 wherein the therapeutic molecule is administered to an artery which serves the kidneys.

6. The method of claim 4 wherein the therapeutic molecule is administered in an amount sufficient to prevent deposition of glycated albumin in renal extracellular matrix of the patient.

7. The method of claim 4 wherein the patient has eye disease.

8. The method of claim 4 wherein the patient has vascular disease.

9. The method of claim 4 wherein the patient has nerve disease.

* * * * *